US010285947B2

(12) United States Patent
Spira et al.

(10) Patent No.: US 10,285,947 B2
(45) Date of Patent: *May 14, 2019

(54) LYOPHILIZED PREPARATIONS OF MELPHALAN FLUFENAMIDE

(71) Applicant: ONCOPEPTIDES AB, Stockholm (SE)

(72) Inventors: Jack Spira, Tyresö (SE); Fredrik Lehmann, Knivsta (SE)

(73) Assignee: Oncopeptides AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/149,975

(22) Filed: May 9, 2016

(65) Prior Publication Data

US 2016/0271065 A1 Sep. 22, 2016

Related U.S. Application Data

(62) Division of application No. 14/438,473, filed as application No. PCT/SE2013/051246 on Oct. 24, 2013.

(60) Provisional application No. 61/719,184, filed on Oct. 26, 2012.

(30) Foreign Application Priority Data

Oct. 26, 2012 (SE) ..................................... 1251211

(51) Int. Cl.

| A61K 38/00 | (2006.01) |
|---|---|
| A61K 9/19 | (2006.01) |
| A61K 38/05 | (2006.01) |
| A61K 47/26 | (2006.01) |
| A61K 31/223 | (2006.01) |
| A61K 47/10 | (2017.01) |

(52) U.S. Cl.
CPC .............. *A61K 9/19* (2013.01); *A61K 31/223* (2013.01); *A61K 38/05* (2013.01); *A61K 47/10* (2013.01); *A61K 47/26* (2013.01)

(58) Field of Classification Search
None
See application file for complete search history.

(56) References Cited

U.S. PATENT DOCUMENTS

| 4,997,651 | A | 3/1991 | Poole et al. |
|---|---|---|---|
| 7,754,720 | B2 | 7/2010 | Bondy et al. |
| 2004/0034099 | A1 | 2/2004 | Ramsey |
| 2004/0097421 | A1 | 5/2004 | Lewensohn et al. |
| 2014/0038996 | A1 | 2/2014 | Inghelbrecht et al. |
| 2014/0128462 | A1 | 5/2014 | Spira et al. |
| 2015/0335578 | A1 | 11/2015 | Spira et al. |

FOREIGN PATENT DOCUMENTS

| CN | 101584669 A | 11/2009 |
|---|---|---|
| EP | 2 599 484 A1 | 6/2013 |
| WO | WO 01/96367 A1 | 12/2001 |
| WO | 2003/077882 | 9/2003 |
| WO | 2004/103274 | 12/2004 |
| WO | 2005/025499 | 3/2005 |
| WO | 2006/066949 | 6/2006 |
| WO | 2007/052076 | 5/2007 |
| WO | 2011/078782 | 6/2011 |
| WO | WO 2012/146625 A1 | 11/2012 |

OTHER PUBLICATIONS

International Preliminary Report on Patentability and Written Opinion of the International Searching Authority (Forms PCT/IB/326, PCT/IB/373 and PCT/ISA/237), dated Nov. 7, 2013, for International application No. PCT/EP2012/057577.
International Search Report dated Jun. 5, 2012 in PCT/EP2012/057577.
Wickstrom, 2007, "Preclinical Studies of the Melphalan Prodrug J1 for Cancer Therapy," Acta Universitatis Upsaliensis. Digital Comprehensive Summaries of Uppsala Dissertations from the Faculty of Medicine 285. 59 pp. Uppsala.
English translation of CN 101584669A, published Nov. 25, 2009.
Baheti et al., "Excipients used in lyophilization of small molecules", Journal of Excipients and Food Chemicals, 2010, vol. 1, No. 1, pp. 41-54, whole document.
International Preliminary Report on Patentability, issued in PCT/SE2013/051246, dated Feb. 9, 2015.
International Search Report, issued in PCT/SE2013/051246, dated Feb. 7, 2014.
Nema et al., "Excipients and Their Use in Injectable Products", PDA Journal of Pharmaceutical Science & Technology, 1997, vol. 51, No. 4, pp. 166-171, p. 169, left-hand column.
Fu et al., eds., 2008, "Auxiliary Materials in lyophilized preparations," Chapter 11 in *The Science of Auxiliary Materials in Pharmaceutics*, Press of Chinese Traditional Medicine (with English translation).
Zezhao Hua, ed., 2005, "Protective agents and additives for freeze drying," pp. 198-199 of Chapter 8 in *New Technology of Freeze Drying*, Science Press, Beijing (with English translation).
Allison et al., 1999, "Hydrogen Bonding between Sugar and Protein is Responsible for Inhibition of Dehydration-Induced Protein Unfolding," Archives of Biochemistry and Biophysics 365(2):289-98.
AmBisome® product insert, 2012, pp. 1-27.
Arshinova et al., 2013, "Adjuvant substances in the freeze-drying technology of medicaments," Scientific and Production Magazine 1(2):20-24 (with English translation).
Barley, "Basic Principles of Freeze Drying," downloaded from https://www.spscientific.com/freeze-drying-lyophilization-basics/ on Mar. 13, 2018.
Bedu-Addo, 2004, "Understanding Lyophilization Formulation Development," Pharmaceutical Technology Lyopilization, pp. 10-18.
Gullbo et al., 2003, "Structure-Activity Relationship for Alkylating Dipeptide Nitrogen Mustard Derivatives," Oncology Research 14:113-132.
Hughes, 2011, "Principles of Early Drug Discovery," British Journal of Pharmacology 162:1239-1249.

(Continued)

*Primary Examiner* — Thomas S Heard
(74) *Attorney, Agent, or Firm* — Biospark Intellectual Property Law

(57) ABSTRACT

The present invention is directed to lyophilized pharmaceutical preparations comprising melphalan flufenamide, or pharmaceutically acceptable salts thereof, methods for their preparation, compositions comprising the lyophilized pharmaceutical preparations and their use in the treatment of cancer.

34 Claims, No Drawings

(56) References Cited

OTHER PUBLICATIONS

Ingvarsson et al., 2011, "Stabilization of liposomes during drying," Expert Opin. Drug Deliv. 8(3):375-388.
Kasraian and DeLuca, 1995, "The Effect of Tertiary Butyl Alcohol on the Resistance of the Dry Product Layer During Primary Drying," Pharmaceutical Research 12(4):491-495.
Lomas et al. 1997, "Commercial plasma $\alpha_1$-antitrypsin (Prolastin®) contains a conformationally inactive, latent component," Eur Respir J. 10:672-675.
Melphanan, DrugBank 2017, downloaded from https://www.drugbank.ca/drugs/DB01042 on Feb. 27, 2017, pp. 1-11.
Melphanan Flufenamide, CAS#380449514, Alkylating Agent, MedKoo, 2017, downloaded from http://www.medkoo.com/products/7959 on Feb. 19, 2017, pp. 1-5.
Nehate et al., 2014, "Paclitaxel Formulations: Challenges and Novel Delivery Options," Curr. Drug Deliv. 11(6):666-86.
Page 3-251 from *Approved Drug Products with Therapeutic Equivalence Evaluations*, 37th ed., 2017 (FDA's Orange Book).
Pilaniya, 2010, "Recent trends in the impurity of profile of pharmaceuticals," J Adv Pharm Technol Rse. 1(3):302-310.
Prescribing information for Alkeran® for Injection, 2002, pp. 1-11.
Prescribing information for Alkeran® tablets, downloaded from https://www.accessdata.fda.gov/drugsatfda_docs/label/2011/0146915029lbl.pdf on Mar. 15, 2018.
Rowe et al., 2006, "Sucrose," in *Handbook of Pharmaceutical Excipients*, fifth ed., pp. 744-747.
Yu et al., 2005, "Freeze drying (lyophilization) of genetic engineering pharmaceuticals," Chinese Journal of Bioprocess Engineering, 5:58-63 (with English translation).
Zezhao Hua, 2005, "Freeze-drying Protectants and Additives," pp. 179-213 of Chapter 8 in *Novel Freeze-Drying Technologies*, Science Press, Beijing (entire chapter with English translation).
First Office Action dated Mar. 1, 2016 in connection with Japanese Patent Application No. 2014-506850 (with English translation).
Decision of Patent dated Oct. 11, 2016 in connection with Japanese Patent Application No. 2014-506850 (including English translation).

LYOPHILIZED PREPARATIONS OF MELPHALAN FLUFENAMIDE

This application is a Divisional of copending application Ser. No. 14/438,473, filed on Apr. 24, 2015, which is a National Phase of PCT International Application No. PCT/SE2013/051246, filed on Oct. 24, 2013, which claims the benefit under 35 U.S.C. § 119(e) to U.S. Provisional Application No. 61/719,184, filed on Oct. 26, 2012, and under 35 U.S.C. § 119(a) to Patent Application No. 1251211-7, filed in SWEDEN on Oct. 26, 2012, all of which are hereby expressly incorporated by reference into the present application.

TECHNICAL FIELD

The present invention is directed to lyophilized pharmaceutical preparations comprising melphalan flufenamide, or pharmaceutically acceptable salts thereof, methods for their preparation, compositions comprising the lyophilized pharmaceutical preparations and their use in the treatment of cancer.

BACKGROUND ART

Cancer is a disease which is difficult to cure and which may be fatal. Accordingly, efforts to develop new therapies for cancer are constantly ongoing in the research society. The vast majorities of cancers are present as solid tumors, e.g. lung cancer, breast cancer, prostate cancer, while the rest are hematological and lymphoid malignancies, e.g. leukemias and lymphomas.

Chemotherapy is often used in attempts to cure or palliate the disease. As cancer cells typically divide rapidly, chemotherapy usually acts by killing rapidly dividing cells. In the broad sense, most chemotherapeutic drugs work by impairing mitosis (i.e. cell division), effectively targeting fast-dividing cells. As these drugs cause damage to cells they are termed cytotoxic. Some drugs cause cells to undergo apoptosis (so-called "programmed cell death"). Often combination chemotherapy is used, when two or more drugs having different modes of action are used together in order to optimise the antitumoral effect, to minimise side effects, and prevent resistance development. The results obtained with chemotherapy vary according to tumor type. Some tumors are very sensitive and the treatment has then a high probability of leading to cure.

Chemotherapeutic drugs can generally be divided into alkylating agents, antimetabolites, anthracyclines, plant alkaloids, topoisomerase inhibitors, and other antitumor agents. The drugs affect cell division or DNA synthesis.

Alkylating agents, such as drugs derived from nitrogen mustard, that is bis(2-chloroethyl)amine derivatives, are used as chemotherapeutic drugs in the treatment of a wide variety of neoplastic diseases. Alkylating agents have the ability to covalently attach alkyl groups to electronegative sites in cells. Thus, these agents act by impairing cell function by forming covalent bonds with heteroatoms in biologically important molecules like RNA, DNA and proteins. Examples of alkylating agents are mechlorethamine, cyclophosphamide, chlorambucil, ifosfamide, temozolomide and melphalan that chemically modify a cell's DNA.

WO01/96367 discloses alkylating di- and tripeptides and one or two additional amino acids or amino acid derivatives. These derivatives were demonstrated to have an improved efficacy on a variety of tumor types.

Lyophilization or freeze-drying is a method for dehydrating samples used to preserve or increase stability or to stop degradation. Due to the low water content of lyophilized products, typically around 1-4%, the action of microorganisms and enzymes is inhibited and the product life thereby increased. In lyophilization, the sample to be lyophilized is dissolved in an aqueous solution and subsequently frozen after which the surrounding pressure is reduced. The sample is then submitted to sublimation, optionally by the application of heat, in order to sublime the frozen water directly from the solid phase to the gas phase. The final water content in the product is very low, typically around 1% to 4%. Lyophilization is commonly used in the pharmaceutical field in order to increase the shelf life of pharmaceutical products.

SUMMARY OF THE INVENTION

The present invention refers to lyophilized preparations comprising melphalanyl-L-p-fluorophenylalanine ethyl ester, also known as melphalan flufenamide, as well as pharmaceutically acceptable salt thereof, in particular melphalanyl-L-p-fluorophenylalanine ethyl ester hydrochloride, also known as melphalan flufenamide hydrochloride, or J1.

Melphalan flufenamide suffers from a poor solubility in aqueous solutions. Therefore, the use of organic solvents, such as DMA (dimethylacetamide), is necessary in order to dissolve the compound. However, organic solvents are often toxic and may also cause destruction of medical devices used for the administration of the compound to subjects, such as cancer patients. Consequently, to overcome the problems with dissolving and providing the compound in an organic solvent, there is a need for alternative pharmaceutical preparations of melphalan flufenamide having sufficient solubility and an optimized dissolution rate in physiologically acceptable solutions.

One aspect of the present invention is directed to a lyophilized pharmaceutical preparation comprising melphalan flufenamide, or a pharmaceutically acceptable salt thereof; and sucrose as excipient.

Still an aspect of the present invention is a lyophilized pharmaceutical preparation which is soluble in an aqueous solution.

Still an aspect of the invention is a kit of parts, comprising a first container comprising a lyophilized pharmaceutical preparation as defined herein, and a second container comprising a physiologically acceptable solution.

Still an aspect of the present invention is a lyophilized pharmaceutical preparation as herein described, for use as a medicament.

Yet an aspect of the invention is a kit of parts as herein described, for use as a medicament.

An aspect of the present invention is a lyophilized pharmaceutical preparation as herein described, for use in the treatment and/or prevention of cancer, such as ovarian cancer, lung cancer, bladder cancer, mesothelioma, multiple myeloma, breast cancer, and/or any solid or hematological cancer.

Yet an aspect of the invention is a kit of parts as herein described, for use in the treatment and/or prevention of cancer, such as ovarian cancer, lung cancer, bladder cancer, mesothelioma, multiple myeloma, breast cancer, and/or any solid or hematological cancer.

Still an aspect of the present invention is a method for the treatment of and/or prevention of cancer, such as ovarian cancer, lung cancer, bladder cancer, mesothelioma, multiple myeloma, breast cancer, and/or any solid or hematological cancer, whereby a lyophilized pharmaceutical preparation as described herein, is administered in a therapeutically effective dose to a subject in need thereof.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will supersede. In addition, the materials, methods, and examples are illustrative only and not intended to be limiting.

Other features and advantages of the invention will be apparent from the following detailed description, examples, and from the claims.

DETAILED DESCRIPTION OF THE INVENTION

Melphalan flufenamide or pharmaceutically acceptable salts thereof has a low solubility in aqueous solutions, which may necessitate the use of organic solvents, such as DMA (dimethylacetamide), for dissolving said compound or pharmaceutically acceptable salts thereof. Therefore, when melphalan flufenamide is to be administered to a patient, the substance first has to be dissolved in an organic solvent, such as DMA, and thereafter diluted in a solution for infusion before administration to the patient. The patient is by this method exposed to organic solvents, the exposure of which may be hazardous for the patient. Also, the organic solvent may destroy the medical devices used for the administration of melphalan flufenamide to subjects, such as cancer patients.

The present inventors have now surprisingly found that when melphalan flufenamide or pharmaceutically acceptable salts thereof is lyophilized in the presence of sucrose, the resulting lyophilized pharmaceutical preparation has a high solubility in a physiologically acceptable solution and further, the dissolution rate is high, which may be beneficial in order to prevent degradation of melphalan flufenamide during dissolution prior to and during administration to a patient.

In previous preparations, melphalan flufenamide was obtained from synthesis as a white powder in crystalline form. This crystalline form can only be dissolved in highly acidic aqueous solutions, which for practical manufacturing purposes is impossible. The presence of excipients as such, did not sufficiently improve the solubility. Therefore, previously melphalan flufenamide was instead dissolved in DMA (dimethylacetamide) in a glucose solution. The preparation is feasible but is unstable: 7% degradation/h. Furthermore, dimerization occurs and the solution turns bright yellow. This preparation was, however, unreliable and the polymerization rate varied in an unacceptable manner.

Consequently, there is a need for identifying alternative ways of providing a preparation comprising melphalan flufenamide or a pharmaceutically acceptable salt thereof that is soluble, with sufficient dissolution rate and with increased stability. Further, the preparation should be water-soluble to avoid negative issues of having an organic solvent in the product that is provided to the patient (such as DMA).

In one aspect of the invention, there is provided a lyophilized pharmaceutical preparation comprising melphalan flufenamide, or a pharmaceutically acceptable salt thereof, and sucrose.

In one embodiment of this aspect, said melphalan flufenamide is melphalan flufenamide hydrochloride (J1).

In another embodiment of this aspect, the weight ratio (w/w) between said melphalan flufenamide and sucrose is from about 1:2 to about 1:500.

In another embodiment of this aspect, the weight ratio (w/w) between said melphalan flufenamide and sucrose is selected from about 1:2, about 1:10, about 1:25, about 1:50, about 1:75, about 1:100, or about 1:500.

In another embodiment of this aspect, the weight ratio (w/w) between said melphalan flufenamide and sucrose is from about 1:2 to about 1:75.

In another embodiment of this aspect, the weight ratio (w/w) between said melphalan flufenamide and sucrose is from about 1:2 to about 1:50.

In another embodiment of this aspect, the weight ratio (w/w) between said melphalan flufenamide and sucrose is from about 1:25 to about 1:75.

In another embodiment of this aspect, the weight ratio (w/w) between said melphalan flufenamide and sucrose is about 1:50.

In another embodiment of this aspect, said lyophilized pharmaceutical preparation comprises about 25 mg melphalan flufenamide hydrochloride (J1) and about 1.25 g sucrose.

In another embodiment of this aspect, said lyophilized pharmaceutical preparation comprises about 50 mg melphalan flufenamide hydrochloride (J1) and about 2.5 g sucrose.

In another embodiment of this aspect, said lyophilized pharmaceutical preparation comprises about 15 mg melphalan flufenamide hydrochloride (J1) and about 0.75 g sucrose.

In another embodiment of this aspect, said lyophilized pharmaceutical preparation comprises about 20 mg melphalan flufenamide hydrochloride (J1) and about 1.0 g sucrose.

In another embodiment of this aspect, said lyophilized pharmaceutical preparation comprises about 40 mg melphalan flufenamide hydrochloride (J1) and about 2.0 g sucrose.

In another embodiment of this aspect, said lyophilized pharmaceutical preparation comprises about 55 mg melphalan flufenamide hydrochloride (J1) and about 2.75 g sucrose.

In another embodiment of this aspect, said lyophilized pharmaceutical preparation comprises about 200 mg melphalan flufenamide hydrochloride (J1) or higher, such as about 300 mg, 400 mg, 500 mg, 600 mg, 700 mg or 800 mg melphalan flufenamide hydrochloride (J1). Such preparations may be particularly useful as a high single dose, such as before transplantation.

In another embodiment of this aspect, said lyophilized pharmaceutical preparation is free, or substantially free from organic solvents.

Prior to use, the lyophilized pharmaceutical preparation comprising melphalan flufenamide, or a pharmaceutically acceptable salt thereof, and sucrose, will be diluted in a physiologically acceptable solution, in order to obtain a useful composition. Therefore, in another embodiment of this aspect there is provided a composition comprising a pharmaceutical preparation of melphalan flufenamide according to the invention.

In another embodiment of this aspect, said composition comprises a physiologically acceptable solution. Preferably, said physiologically acceptable solution is a glucose solution. Typically, the amount of glucose is about 4.5-5.5% by weight of the lyophilized preparation.

The invention provides a lyophilized preparation which is stable in dry form and soluble in an aqueous solution without presence of an organic solvent. While it previously was possible to prepare a lyophilized preparation of melphalan flufenamide alone, such preparation dissolved too slowly in aqueous solutions compared to the degradation time. Incorporation of sucrose in the lyophilized melphalan flufenamide preparation (via initial solution in an organic solvent) improves the reconstitution time considerably, but does not significantly alter the stability of reconstituted melphalan flufenamide. As a result, the time window for the reconstituted melphalan flufenamide is widened, and this improves the treatments of patients, e.g. by allowing for lower infusion rates, where needed. A preparation "without presence of an organic solvent" could include trace amounts of organic solvent, typically less than 0.5% (w/w).

The lyophilized pharmaceutical preparation of melphalan flufenamide or a pharmaceutically acceptable salt thereof as described herein, is a white, fluffy powder in contrast to a non-lyophilized melphalan flufenamide or a pharmaceutically acceptable salt thereof, which can be in the form of a dense, slightly yellowish powder.

Typically, lyophilization comprises four steps, pretreatment, freezing, primary drying, and secondary drying. In the pretreatment step, the substance to be lyophilized is made ready for the lyophilization e.g. by preparing a solution having the desired concentration or mixing the substance with further components in order to obtain an acceptable result. The freezing step may be performed in a freeze-drying flask in a bath cooled e.g. by mechanical refrigeration, dry ice and methanol, or liquid nitrogen. Freeze-drying machines are available for lyophilization in a larger scale. Usually, the freezing temperatures are between −50° C. and −80° C.

In the primary drying step, the pressure is lowered to the range of a few millibars, and heat may be supplied for the water to sublimate from the material. The amount of heat necessary can be calculated using the sublimating molecules' latent heat of sublimation. The duration of this period depends, but may last for days in order to preserve the materials structure.

The aim of the final secondary drying step is to remove any unfrozen water molecules. In this phase, the temperature may be as high as above 0° C., to break any physico-chemical interactions that have formed between the water molecules and the frozen material.

In the context of the present invention, it is to be understood that melphalan flufenamide or a pharmaceutically acceptable salt thereof, is lyophilized. The term "a lyophilized pharmaceutical preparation of a melphalan flufenamide or a pharmaceutically acceptable salt thereof", is therefore understood to mean that the melphalan flufenamide or a pharmaceutically acceptable salt thereof is lyophilized.

Further aspects of the present invention provide lyophilized melphalan flufenamide or a pharmaceutically acceptable salt thereof, a kit of parts comprising such melphalan flufenamide, methods for the preparation of such melphalan flufenamide or a pharmaceutically acceptable salt thereof, compositions comprising such lyophilized melphalan flufenamide or a pharmaceutically acceptable salt thereof and uses thereof.

"Lyophilization", "lyophilized" etc. may in the present context be used interchangeably with "freeze-drying", "freeze-dried" etc.

Melphalan flufenamide may also contain unnatural proportions of atomic isotopes at one or more of its atoms, such as deuterium ($^2H$). The compounds may be radiolabeled with radioactive isotopes, such as for example tritium ($^3H$), iodine-125 ($^{125}I$) or carbon-14 ($^{14}C$).

The inclusion of sucrose provides lyophilized preparation that is stable as such and water-soluble without the presence of an organic solvent at a sufficient rate compared to the degradation rate, and is thereby useful in therapy and is less toxic.

Pharmaceutically acceptable salts for all aspects of the present invention may be, for instance, an acid-addition salt of a compound described herein which is sufficiently basic, for example, an acid-addition salt with, for example, an inorganic or organic acid, for example hydrochloric, hydrobromic, nitric, methansulphonic, sulphuric, phosphoric, trifluoroacetic, para-toluene sulphonic, 2-mesitylen sulphonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid.

In this document, when the term "melphalan flufenamide" is used, it is also intended to include pharmaceutically acceptable salt(s) thereof, even if this is not explicitly stated.

As mentioned hereinbefore, when melphalan flufenamide or a pharmaceutically acceptable salt thereof is lyophilized in the presence sucrose, an unexpectedly high increase in solubility of the lyophilized pharmaceutical preparation can be obtained, which enables the direct dissolution of the lyophilized melphalan flufenamide in an aqueous solution, such as a physiologically acceptable solution. This is in contrast to a non-lyophilized melphalan flufenamide which is not possible to dissolve directly in an aqueous solution but that first has to be dissolved in an organic solvent prior to dilution in an aqueous solution. It is therefore provided herein a lyophilized pharmaceutical preparation comprising melphalan flufenamide or a pharmaceutically acceptable salt thereof, wherein melphalan flufenamide is lyophilized in the presence of sucrose.

Due to a low solubility of non-lyophilized melphalan flufenamide in aqueous physiologically acceptable solutions used for administration of the drug to a patient, it is necessary to first dissolve the non-lyophilized melphalan flufenamide in an organic solvent, such as DMA. Melphalan flufenamide is therefore often stored dissolved in DMA. It has previously not been possible to directly dissolve the melphalan flufenamide in an aqueous solution, but organic solvents have had to be used. Once dissolved in the organic solvent, this solution of melphalan flufenamide and organic solvent can be dissolved in physiologically acceptable solutions for administration to a subject.

As melphalan flufenamide is very toxic, in order to minimize the exposure of medical personnel to such drugs, special devices for transferring the drugs after dissolution in organic solvents to the solution for administration, are used. These transfer devices are often plastic tubings comprising polycarbonate. However, such tubings are sensitive to and may be destroyed by organic solvents, such as DMA. Therefore, in the cases where the drug to be administered is dissolved in such an organic solvent, it may not be possible to use the transfer device, and the dissolved drug instead has to be directly added to the physiologically acceptable solution used for administration just before the time of administration to the patient. This can be hazardous for the medical staff, who then are at risk being exposed to the toxic drug.

As mentioned above, lyophilization of melphalan flufenamide increases its solubility in physiologically acceptable solutions. This increase can be even more pronounced when melphalan flufenamide is lyophilized in the presence of sucrose. As described herein, when melphalan flufenamide is lyophilized in the presence of sucrose, the solubility of melphalan flufenamide can be increased, in comparison to the non-lyophilized melphalan flufenamide. The use of an organic solvent, such as DMA, to first dissolve melphalan flufenamide can be avoided.

Melphalan flufenamide which has been lyophilized in the presence of sucrose, can be directly dissolved in a physiologically acceptable solution, such as about 4.5-5.5 wt %, e.g. about 5%, glucose solution or an aqueous NaCl solution (e.g. about 0.9 wt % NaCl). Thereby, devices comprising polycarbonate and which are used for the administration of melphalan flufenamide are possible to use, minimizing the risk for exposing the medical personnel to the drug. Also, in this way administering the toxic DMA to the patient is avoided. This allows for directly preparing the solution comprising melphalan flufenamide at a concentration suitable for administration to the patient. Alternatively, a concentrated solution comprising a lyophilized pharmaceutical preparation of melphalan flufenamide in a physiologically acceptable solution may first be prepared and then transferred to the bag for infusion using the commonly used transfer devices.

Also, when melphalan flufenamide is dissolved in DMA, an adduct between the melphalan flufenamide and the DMA typically is formed. By using a lyophilized pharmaceutical preparation provided in accordance with the invention, it is possible to dissolve the lyophilized melphalan flufenamide directly in a physiologically acceptable solution, avoiding first dissolving the melphalan flufenamide in DMA. Thereby, the formation of a DMA-melphalan flufenamide adducts can be avoided and neither the adduct nor the DMA have to be administered to the patient.

There is also provided a pharmaceutical composition comprising a lyophilized pharmaceutical preparation of melphalan flufenamide or pharmaceutically acceptable salt thereof as defined herein, optionally obtainable by the method for preparing such a lyophilized preparation disclosed herein. Such a pharmaceutical composition may further comprise a physiologically acceptable solution, such as an aqueous NaCl (e.g. about 0.9 wt %) or glucose solution (e.g. 4.5-5.5 wt %, such as about 5 wt %, glucose). This pharmaceutical composition may be a concentrated solution intended for dilution before administration to a subject or as a solution enabling direct administration to a patient.

Due to the increased solubility of melphalan flufenamide after lyophilization in the presence of sucrose as described herein, it is possible to prepare a dissolved melphalan flufenamide solution, such as a pharmaceutical composition comprising a melphalan flufenamide or pharmaceutically acceptable salt thereof, which is substantially free from organic solvents such as DMA, dichloromethane, tetrahydrofuran, 2-methyl tetrahydrofuran, ethyl acetate, acetone, dimethylformamide, acetonitrile, dimethyl sulfoxide, dioxane, diethyl ether, acetic acid, n-butanol, isopropanol, n-propanol, tert-butanol, sec-butanol, methanol, ethanol, and acetic acid.

By "substantially free" is in this document meant that the pharmaceutical composition comprises only trace amounts of an organic solvent, such as less than about a total of about 1 wt % of an organic solvent, preferably less than about a total of about 0.5 wt % of an organic solvent, more preferably less than about a total of about 0.1 wt % of an organic solvent. In one aspect, the lyophilized preparation or the pharmaceutical composition does not contain any measurable amounts of an organic solvent. Such preparations would be less toxic and therefore more tolerated by a patient, i.e. giving less side effects such as vomiting, nausea or other general symptoms when infused.

In one aspect of the invention, there is provided a lyophilized pharmaceutical preparation as described herein, which is free, or substantially free from organic solvents.

The pharmaceutical composition may consist of a lyophilized pharmaceutical preparation as disclosed herein, comprising melphalan flufenamide or pharmaceutical salt thereof, and the physiologically acceptable solution, such as a glucose solution.

The wording a "physiologically acceptable solution" is herein defined, is an aqueous solution, such as a NaCl solution (such as about 0.9 wt-% NaCl) or glucose solution, such as about 4.5-5.5 wt-% glucose, e.g. about 5 wt-%, or another physiologically acceptable solution. Any such solution may optionally be buffered.

A pharmaceutical composition comprising lyophilized melphalan flufenamide and a physiologically acceptable solution for direct administration to a subject, generally comprises melphalan flufenamide at a concentration of about 1 mg/ml or less, such as about 0.2 mg/ml. However, the pharmaceutical composition may comprise melphalan flufenamide in a concentration of up to about 4 mg/ml for dilution in a physiologically acceptable solution before administration to a patient.

Another aspect of the invention provides a method for preparing a lyophilized pharmaceutical preparation, whereby:
a. melphalan flufenamide, or a pharmaceutically acceptable salt thereof, is dissolved in an organic solvent to obtain a melphalan flufenamide solution;
b. the melphalan flufenamide solution is added to sucrose to obtain an aqueous melphalan flufenamide/sucrose solution; and
c. the aqueous melphalan flufenamide/sucrose solution is subjected to lyophilization.

In one embodiment of this aspect, the weight ratio (w/w) between said melphalan flufenamide and sucrose is from about 1:2, about 1:10, about 1:25, about 1:50, about 1:75, about 1:100, or about 1:500.

In another embodiment of this aspect, the weight ratio (w/w) between said melphalan flufenamide and sucrose is from about 1:2 to about 1:50.

In another embodiment of this aspect, the weight ratio (w/w) between said melphalan flufenamide and sucrose is about 1:50.

In another embodiment of this aspect, there is provided a method, wherein the weight ratio (w/w) between said melphalan flufenamide and sucrose is from about 1:25 to about 1:75. Preferably, the weight ratio (w/w) between said melphalan flufenamide and sucrose is about 1:50.

The organic solvent may be selected from any one of ethanol, ethanol containing acid, glycerin, propylene glycol, benzyl alcohol, dimethylacetamide (DMA), N-methyl-2-pyrrolidone, isopropanol, n-butanol, tert-butanol, methyl tert-butyl ether, propylene glycol, dimethylsulfoxide, tetrahydrofuran, 2-methyl tetrahydrofuran, acetone, dimethylformamide, acetonitrile, dioxane, acetic acid, lactic acid, propionic acid, n-butanol, isopropanol, n-propanol, tert-butanol, a mixture of tert-butanol and water, sec-butanol, methanol, and a mixture of ethanol and water. Preferably, said organic solvent is tert-butanol or a mixture of tert-butanol and water, more preferably a mixture of tert-butanol and water at a volume ratio of about 1:1.

Another aspect of the present invention is a method for the preparation of a lyophilized pharmaceutical preparation as herein described, whereby
a) melphalan flufenamide, or a pharmaceutically acceptable salt thereof, is dissolved in an organic solvent;
b) water is added to the solution obtained in step a) in order to obtain a solution of said melphalan flufenamide or a pharmaceutically acceptable salt thereof, in a concentration of about 0.2-3.0 mg/ml;
c) sucrose is added to the solution obtained in step b); and
d) the solution obtained in step c) is subjected to lyophilization.

Preferably, said organic solvent is tert-butanol.

Another aspect of the present invention is a method for the preparation of a lyophilized pharmaceutical preparation as herein described, whereby
a) melphalan flufenamide hydrochloride (J1), is dissolved in a 1:1 (v/v) mixture of tert-butanol and water to obtain a solution;
b) the solution in step a) is added to lyophilized sucrose, to obtain a solution of melphalan flufenamide hydrochloride (J1), tert-butanol, water and sucrose; and
c) the solution obtained in step c) is subjected to lyophilization.

Examples of organic solvents useful for dissolving melphalan flufenamide, or a pharmaceutically acceptable salt thereof in step a), may be any one selected from ethanol, ethanol containing acid, glycerin, propylene glycol, benzyl alcohol, dimethylacetamide (DMA), N-methyl-2-pyrrolidone, isopropanol, n-butanol, tert-butanol, methyl tert-butyl ether, propylene glycol, dimethylsulfoxide, tetrahydrofuran, 2-methyl tetrahydrofuran, acetone, dimethylformamide, acetonitrile, dioxane, acetic acid, lactic acid, propionic acid, n-butanol, isopropanol, n-propanol, tert-butanol, a mixture of tert-butanol and water, sec-butanol, methanol, and a mixture of ethanol and water.

When melphalan flufenamide or a pharmaceutically acceptable salt thereof is dissolved in tert-butanol and water, the concentration of tert-butanol may be about 10-100 vol-%, such as 10-90 vol-%, 30-70 vol-%, or about 50 vol-%.

The water used for dissolving and/or diluting samples of a lyophilized pharmaceutical preparation in accordance with the present invention, is sterile or purified water, or water for injection (WFI).

Information about how lyophilization is performed may be found e.g. in Rey, L. and May, *J. Freeze Drying/Lyophilization of Pharmaceutical and Biological Products* (2010), ISBN 978-1439B2575-4. In the freezing step, the sample is for example frozen in a bath of dry ice-acetone at a temperature of about −70° C. to −90° C., such as about −70° C., −75° C., −78° C., −80° C., −82° C., −85° C., −88° C. or −90° C. for example for 10 minutes to 120 minutes.

Alternatively, the sample may be frozen in a freezer at a temperature about −14° C. to −25° C., such as −14° C., −16° C., −18° C., −20° C., −22° C., or −25° C., for example for about 10 min to 24 hours. It is also possible to freeze the sample in liquid nitrogen.

In the primary freeze-drying step, the pressure can be lowered to about to about 0.1 mbar to 50 mbar, such as 1 mbar to 10 mbar. The temperature is typically below 0° C., such as −50 to 0° C., or −20 to −1° C., e.g. −50, −40, −30, −20, −10, or −5° C. This phase may for example last for 4 hours to 48 hours, e.g. 12 hours to 24 hours.

In the final drying step, when most of the water has evaporated, the temperature may be as in the primary drying step or above 0° C.

Sucrose can be added prior to or after diluting the solution obtained in step a) and prior to performing the lyophilization. Sucrose is typically in powder form but may be added as an aqueous solution.

The present invention is also directed to a lyophilized pharmaceutical preparation as defined herein obtainable by the above disclosed method.

It is also provided herein a kit of parts combination comprising:
(i) a first container comprising a lyophilized pharmaceutical preparation comprising melphalan flufenamide as described herein; and
(ii) a second container comprising a physiologically acceptable solution, such as a NaCl solution (such as about 0.9 wt % NaCl) or a glucose solution, such as about 4.5-5.5 wt % glucose solution, e.g. about 5 wt % glucose solution, or other physiologically acceptable solution.

Such a kit may also comprise a device for mixing the contents of the two containers with each other and/or for transferring the resulting mixture to a device, such as a bag comprising a glucose solution, for the administration to a patient.

Such a kit may consist of the first container comprising a lyophilized pharmaceutical preparation comprising melphalan flufenamide as described herein and the second container comprising the physiologically acceptable solution. Melphalan flufenamide in the kit may also be in admixture with a pharmaceutically acceptable carrier and/or excipient. One example is 5% glucose with e.g. 1% albumin or another protein or compound. The amount of physiologically acceptable solution may either be a small amount in order to prepare a concentrated solution of the lyophilized pharmaceutical preparation comprising melphalan flufenamide, or a larger amount in order to enable the preparation of a solution having the desired concentration for administration to a patient. Alternatively, the kit may comprise both a container comprising a physiologically acceptable solution for preparing a concentrated solution of the lyophilized pharmaceutical preparation and a second container, such as a bag for infusion, comprising a larger amount of a physiologically acceptable solution for preparation of the more diluted solution for administration to a subject.

A lyophilized pharmaceutical preparation, pharmaceutical composition or kit provided herein may comprise only melphalan flufenamide or a pharmaceutically acceptable salt thereof as an antitumoral agent. However, melphalan flufenamide may also be combined with one or more antitumoral agents, such as other antitumoral substances such as gemcitabine, etoposide, doxorubicine or taxanes or other therapeutically effective substances. When combined with other antitumoral agents these may either be mixed with melphalan flufenamide or pharmaceutically acceptable salt thereof before lyophilisation and consequently lyophilized together with melphalan flufenamide or pharmaceutically acceptable salt thereof or combined with the lyophilized melphalan flufenamide or pharmaceutically acceptable salt thereof after lyophilisation, such as in a kit or a pharmaceutical composition. Lyophilized melphalan flufenamide may also be mixed with one or more antitumoral substances in dry form, even though not lyophilized, after lyophilisation of melphalan flufenamide or pharmaceutically acceptable salt thereof.

Melphalan flufenamide provided herein have a cytotoxic activity and may therefore be used in the prevention and/or treatment of cancer as described elsewhere (see e.g. WO 01/96367). A reduction of tumor cell survival of melphalan flufenamide was in WO 01/96367 demonstrated for different hematological and/or solid tumors, e.g. lung cancer, myeloma, lymphoma, leukemia, breast cancer, and ovarian carcinoma. Further, melphalan flufenamide was in WO 01/96367 demonstrated to circumvent melphalan resistance. Melphalan flufenamide may therefore be used in the prevention and/or treatment of cancer, reducing tumor growth and/or killing tumor cells. Thus, melphalan flufenamide may be used for curing and/or prolonging the survival of patients afflicted with cancer diseases. Melphalan flufenamide may also be used as a high single dose, before transplantation, of a cancer patient Another aspect of the present invention provides use of a lyophilized pharmaceutical preparation, kit or pharmaceutical composition as disclosed and claimed herein, for use as a medicament.

Another aspect of the present invention provides use of a lyophilized pharmaceutical preparation, kit or pharmaceutical composition as disclosed and claimed herein, for use in the treatment and/or prevention of cancer, such as ovarian cancer, lung cancer, bladder cancer, mesothelioma, multiple myeloma, breast cancer and/or any other solid or hematological cancer.

In one embodiment of this aspect, said lyophilized pharmaceutical preparation, kit or pharmaceutical composition as disclosed and claimed herein, for use in the treatment and/or prevention of cancer, such as ovarian cancer, lung cancer, bladder cancer, mesothelioma, multiple myeloma, breast cancer and/or any other solid or hematological cancer, is provided every $3^{rd}$ week, typically for 3 to 6 treatment cycles.

Another aspect of the present invention provides use of a lyophilized pharmaceutical preparation, kit or pharmaceutical composition as disclosed and claimed herein, for use before transplantation of cancer, such as ovarian cancer, lung cancer, bladder cancer, mesothelioma, multiple myeloma, breast cancer and/or any other solid or hematological cancer. In such use, the preparation comprises about 200 mg melphalan flufenamide hydrochloride (J1) or higher, such as about 300 mg, 400 mg, 500 mg, 600 mg, 700 mg or 800 mg melphalan flufenamide hydrochloride (J1). Such preparations may be particularly useful as a high single dose, before transplantation.

Another aspect of the present invention provides use of a lyophilized pharmaceutical preparation, kit or pharmaceutical composition as disclosed and claimed herein, for the preparation of a medicament for the treatment and/or prevention of cancer, such as ovarian cancer, lung cancer, bladder cancer, mesothelioma, multiple myeloma, breast cancer and/or any other solid or hematological cancer.

Another aspect of the present invention provides use of a lyophilized pharmaceutical preparation, kit or pharmaceutical composition as disclosed and claimed herein, for the preparation of a medicament before transplantation of cancer, such as ovarian cancer, lung cancer, bladder cancer, mesothelioma, multiple myeloma, breast cancer and/or any other solid or hematological cancer. In such use, the preparation comprises about 200 mg melphalan flufenamide hydrochloride (J1) or higher, such as about 300 mg, 400 mg, 500 mg, 600 mg, 700 mg or 800 mg melphalan flufenamide hydrochloride (J1). Such preparations may be particularly useful as a high single dose, before transplantation.

Another aspect of the present invention provides a lyophilized pharmaceutical preparation, kit or pharmaceutical composition comprising melphalan flufenamide hydrochloride (J1) in combination with another drug useful in the treatment of cancer, for use in treatment and/or prevention of cancer, such as ovarian cancer, lung cancer, bladder cancer, mesothelioma, multiple myeloma, breast cancer and/or any other solid or hematological cancer.

Yet an aspect of the present invention is a method for the treatment of and/or prevention of cancer, such as ovarian cancer, lung cancer, bladder cancer, mesothelioma, multiple myeloma, breast cancer and/or any other solid or hematological cancer. The method can comprise the administration of a lyophilized pharmaceutical preparation, a kit or a pharmaceutical composition as provided herein in a therapeutically effective dose to a subject in need thereof. The subject is typically a human or a domestic animal.

In one embodiment of this aspect, the lyophilized pharmaceutical preparation, a kit or a pharmaceutical composition as provided herein in a therapeutically effective dose to a subject in need thereof every $3^{rd}$ week typically for 3 to 6 treatment cycles.

Yet an aspect of the present invention is a method for the treatment of and/or prevention of cancer, such as ovarian cancer, lung cancer, bladder cancer, mesothelioma, multiple myeloma, breast cancer and/or any other solid or hematological cancer, wherein the lyophilized pharmaceutical preparation, a kit or a pharmaceutical composition comprising melphalan flufenamide hydrochloride (J1) is provided in a therapeutically effective dose to a subject in need thereof, in combination with another drug, useful in the treatment of cancer. The subject is typically a human or a domestic animal.

Yet an aspect of the present invention is a method for the treatment of and/or prevention of cancer, such as ovarian cancer, lung cancer, bladder cancer, mesothelioma, multiple myeloma, breast cancer and/or any other solid or hematological cancer, wherein the lyophilized pharmaceutical preparation, a kit or a pharmaceutical composition comprising melphalan flufenamide hydrochloride (J1) is provided in a therapeutically effective dose before transplantation to a subject in need thereof. The subject is typically a human or a domestic animal. In such a method, the preparation comprises about 200 mg melphalan flufenamide hydrochloride (J1) or higher, such as about 300 mg, 400 mg, 500 mg, 600 mg, 700 mg or 800 mg melphalan flufenamide hydrochloride (J1). Such preparations may be particularly useful as a high single dose, before transplantation.

The administration of a lyophilized pharmaceutical preparation, a kit or a pharmaceutical composition to a subject in need thereof may take place by intravenous injections. It is also possible to administer lyophilized melphalan flufenamide or a pharmaceutical composition comprising such lyophilized melphalan flufenamide in body cavities, such as instillation in the bladder, or in peritoneal or pleural cavities.

Melphalan flufenamide or a pharmaceutically acceptable salt thereof may be administered in an amount of about 20-130 mg, such as 25-75 mg, for example 15, 20, 25, 40, 50 or 55 mg total amount of melphalan flufenamide per administration. The pharmaceutical composition or kit provided herein comprising melphalan flufenamide may therefore have an amount of lyophilized melphalan flufenamide such that this amount can be administered.

Melphalan flufenamide or a pharmaceutically acceptable salt thereof may be administered in an amount of about 20-130 mg, such as 25-75 mg, for example 15, 20, 25, 40, 50 or 55 mg total amount of melphalan flufenamide per administration. The pharmaceutical composition or kit provided herein comprising melphalan flufenamide may therefore have an amount of lyophilized melphalan flufenamide such that this amount can be administered every $3^{rd}$ week, typically for 3 to 6 treatment cycles.

Lyophilized melphalan flufenamide or a pharmaceutically acceptable salt thereof may be administered daily, every second or third day, weekly, every second, third or 4$^{th}$ week or even as a high single dose, such as before transplantation, depending on the subject and cancer form to be treated. A high single dose may be about 200 mg, or higher, of melphalan flufenamide, such as about 300, 400, 500, 600, 700, or 800 mg of melphalan flufenamide.

The wording "prevention" as used herein, is intended to include therapy in a patient that has been subjected to chemotherapy against any cancer form as herein described, and who is subjected to continued therapy with the aim of preventing any methastasis occurring from said cancer.

Yet an aspect of the present invention provides use of sucrose as excipient, in a lyophilized preparation of melphalan flufenamide, or a pharmaceutically acceptable salt thereof, for decreasing the reconstitution time of the lyophilized preparation of said melphalan flufenamide, when reconstituted in an aqueous solvent.

Said melphalan flufenamide, or a pharmaceutically acceptable salt thereof, is preferably melphalan flufenamide hydrochloride (J1).

Said melphalan flufenamide, or a pharmaceutically acceptable salt thereof, is preferably dissolved in tert-butanol or a mixture of tert-butanol and water, prior to subjecting said melphalan flufenamide to said excipient.

In this document "lyophilization", "freeze-drying", "lyophilized", "freeze-dried", and the like may be used interchangeably.

Sucrose is e.g. sold by Dansukker, having the CAS Registry Number 57-50-1.

Yet an aspect of the present invention provides use of tert-butanol, optionally in mixture with water, in a process for preparing a lyophilized pharmaceutical preparation of melphalan flufenamide, preferably melphalan flufenamide hydrochloride (J1). Preferably, said tert-butanol is in mixture with water at a volume ratio of about 1:1.

Melphalan flufenamide, or a pharmaceutically acceptable salt thereof, may be prepared as disclosed in WO 01/96367, which disclosure is incorporated by reference. Example 1 of WO 01/96367 discloses a synthetic procedure for making melphalan flufenamide (L-melphalanyl-L-p-fluorophenylalanine ethyl ester), as well as its hydrochloride salt-melphalan flufenamide hydrochloride J1 (L-melphalanyl-L-p-fluorophenylalanine ethyl ester, compound J1), which disclosure is incorporated herein. In WO 01/96367, melphalan flufenamide was demonstrated to have an increased cell killing activity against tumors, even when used at lower concentrations than melphalan. In addition, melphalan resistance could be circumvented.

The invention will be further described by way of the following examples, which do not limit the scope of the invention.

Example 1. Effect of Sucrose on the Dissolution Rate of Lyophilized Melphalan Flufenamide The speed of dissolution of melphalan flufenamide hydrochloride (J1) by addition of sucrose to the freeze-drying process of J1 was tested. Sucrose is a formulation agent Generally Considered As Safe (GRAS) according to the FDA (US Food and Drug Administration).

Step 1—Preparation and Lyophilization of J1

A solution of J1 (5 mg) was made in tert-butanol:water 1:1 (5 ml). 100 μl of the solution was added to a vial containing 0.2 mg sucrose. The vial was covered with aluminium foil and frozen on dry ice-acetone. The vial consisted of 0.1 mg J1 and 0.2 mg sucrose. The vial with sample was thereafter freeze-dried overnight. Freeze-drying was performed on a Leybold Lyovac GT2 equipment.

Step 2—Glucose Solution for Dissolution

A 5% glucose solution (100 ml) was prepared and the internal marker 3-methoxy-benzoic acid (0.8 mg/ml) was added to the solution.

Step 3—Determination of Dissolution Rate 0.5 ml of the glucose solution from step 2, was added to the freeze-dried vial with J1 sample from step 1. The vial was shaken at room temperature for 15 seconds and thereafter filtered and transferred to a glass vial for J1 concentration measurement, with HPLC. The amount of dissolved J1 was determined using HPLC and a calibration curve.

Results

The concentration of J1, dissolved in the glucose solution during 15 seconds of step 3 was 0.08 mg/ml, which represents approximately 40% of J1 dissolved in 15 seconds.

Example 2. Test of Effect of Amount of Sucrose on the Dissolution Rate of Melphalan Flufenamide in Water Solution The speed of dissolution by addition of sucrose in different amounts to the freeze-drying process of melphalan flufenamide hydrochloride (J1) was tested. The experimentation was carried as set out in Example 1 above but the amount of sucrose was varied: A solution of J1 (5 mg) was made in tert-butanol:water 1:1 (5 ml). 100 μl of the solution was added to vials containing freeze-dried sucrose of 0.2 mg, 5 mg and 50 mg, respectively. The vials were covered with aluminium foil and frozen on dry ice-acetone. The vials consisted of 0.1 mg J1 and 0.2 mg sucrose (ratio 1:2 w/w), 0.1 mg J1 and 5 mg sucrose (ratio 1:50 w/w) and 0.1 mg J1 and 50 mg sucrose (ratio 1:500 w/w). The vials with samples were thereafter freeze-dried overnight. Freeze-drying was performed on a Leybold Lyovac GT2 equipment. A water solution (100 ml) was prepared and the internal marker 3-methoxy-benzoic acid (0.08 mg/ml) was added to the solution. 0.5 ml of the glucose solution was added to each of the freeze-dried vials with J1 sample. The vials were shaken at room temperature for 15 seconds and thereafter filtered and transferred to glass vials for J1 concentration measurement, with HPLC. The amount of dissolved J1 in each vial was determined using HPLC and a calibration curve. The concentration of J1, dissolved in the water solution during 15 seconds for each vial is presented in Table 1.

TABLE 1

| Amount of J1/sucrose | Weight ratio J1:Sucrose (w/w) | % of J1 dissolved in 15 sec |
| --- | --- | --- |
| 0.1 mg/0.2 mg | 1:2 | 46 |
| 0.1 mg/5 mg | 1:50 | 97 |
| 0.1 mg/50 mg | 1:500 | 20 |

The results in Table 1 show that an unexpected increase of dissolution rate occurred when the weight ratio (w/w) between said melphalan flufenamide and sucrose was about 1:50, however, a substantial increase of dissolution rate occurred when the weight ratio (w/w) between said melphalan flufenamide and sucrose was 1:2.

Example 3. Test of Effect of Amount of Sucrose on the Dissolution Rate of Melphalan Flufenamide in Glucose Solution A 1 mg/mL solution of J1 was prepared in tert-butanol/water 1:1. 100 uL of this solution was added to seven 2 mL transparent glass vials containing sucrose (0.2 mg, 1 mg, 2.5 mg, 5.0 mg, 7.5 mg, 10 mg and 50 mg). The glass vials were used such that it could be monitored that a homogeneous mixture had formed between J1 and sucrose before freeze-drying. The vials were occasionally shaken. Vials 1-3 showed a clear solution (visual inspection) after 1-2 minutes while vials 4-7 containing larger amount of sucrose needed up to 20 minutes before all lumps of sugar was dissolved. For vial 6 and 7 a two phase system was observed (t-butanol/water) and a homogeneous solution was not obtained. The 7 vials were cooled and freeze-dried for 36 hours.

A 5% glucose solution containing 0.08 mg/mL of 3-methoxy-benzoic acid (0.5 mL) was added to each of the polypropylene vials containing J1:sucrose lyophilized mixture, one at the time. The vial was shaken at room temperature for 15 seconds, the solution was filtered through a filter device supplied with the vial, and transferred to a glass vial for analysis of J1 concentration with HPLC. Comparing the HPLC integral values for the J1 peaks with a calibration curve, the concentrations in mg/mL could be calculated. The results are shown in Table 2.

TABLE 2

Dissolution of J1 after 15 seconds in a 5% glucose-solution.

| Sample | Area (254 nM) | Area.int.standard (305 nM) | solubility mg/mL (15 sec) | J1:sucrose (w/w) | % J1 dissolved |
|---|---|---|---|---|---|
| 1 | 1120 | 242 | 0.16 | 1:2 | 79 |
| 2 | 998 | 249 | 0.14 | 1:10 | 71 |
| 3 | 1263 | 260 | 0.18 | 1:25 | 90 |
| 4 | 1195 | 254 | 0.17 | 1:50 | 85 |
| 5 | 1173 | 255 | 0.17 | 1:75 | 83 |
| 6 | 513 | 250 | 0.07 | 1:100 | 36 |
| 7 | 1204 | 264 | 0.17 | 1:500 | 85 |

Table 2 shows that the dissolution rate of J1 after 15 seconds are fast for all ratios of sucrose except for sample 6 where only 36% dissolved. As mentioned above, sample 6 and 7 were inhomogeneous before freeze-dying and this could be a plausible explanation.

Example 4. Test of Effect of Amount of Sucrose on the Dissolution Rate of Melphalan Flufenamide in Glucose Solution with Vial Transfer Example 3 above was repeated, however, with the difference that after filtration, the mixture was transferred from the polypropylene filter vial to a glass vial to prevent further dissolution. The results are shown in Table 3.

TABLE 3

Dissolution of J1 after 15 seconds in a 5% glucose-solution.

| Sample | Area (254 nM) | Area.int.standard (305 nM) | solubility mg/mL (15 sec) | J1:sucrose (w/w) | % J1 dissolved |
|---|---|---|---|---|---|
| 1 | 906 | 227 | 0.13 | 1:2 | 64 |
| 2 | 959 | 238 | 0.14 | 1:10 | 68 |
| 3 | 898 | 229 | 0.13 | 1:25 | 63 |
| 4 | 924 | 235 | 0.13 | 1:50 | 65 |
| 5 | 570 | 217 | 0.08 | 1:75 | 40 |
| 6 | 918 | 236 | 0.13 | 1:100 | 65 |
| 7 | 811 | 242 | 0.11 | 1:500 | 57 |

The solubility of J1 was somewhat lower than as described in example 3. Therefore, transfer to a glass vial when conducting these studies could be of importance to prevent further dissolution. Notice that the internal standard is 10% lower in these experiments. This could be explained by the pressure differences in the filter vial versus the glass vial and results in differences in injection volume on the HPLC.

Example 5. Test of Effect of Amount of Sucrose on the Dissolution Rate of Melphalan Flufenamide in Water Solution Further experiments were carried out to investigate the effect of glucose on the dissolution of J1 after 15 seconds. The freeze drying was performed as above, but instead of a 5% glucose solution, a water solution containing 0.08 mg/mL of 3-methoxybenzoic acid (0.5 mL) was added to each of the glass vials, one at the time. The vial was shaken at room temperature for 15 seconds and transferred to a polypropylene vial, filtered, and transferred to a glass vial to prevent further dissolution. The J1 concentration was determined with HPLC. The experiment was run in duplicate (a and b). The results are shown in Table 4.

TABLE 4

Dissolution of J1 after 15 seconds in a water solution.

| Sample | Area (254 nM) | Area.int.standard (305 nM) | solubility mg/mL (15 sec) | J1:sucrose (w/w) | % J1 dissolved |
|---|---|---|---|---|---|
| 1a | 1032 | 205 | 0.15 | J1:Suc 1:2 | 73 |
| 1b | 968 | 209 | 0.14 |  | 68 |
| 2a | 945 | 206 | 0.13 | J1:Suc 1:10 | 67 |
| 2b | 850 | 202 | 0.12 |  | 60 |
| 3a | 876 | 197 | 0.12 | J1:Suc 1:25 | 62 |
| 3b | 879 | 203 | 0.12 |  | 62 |
| 4a | 971 | 209 | 0.14 | J1:Suc 1:50 | 69 |
| 4b | 889 | 204 | 0.13 |  | 63 |
| 5a | 464 | 203 | 0.06 | J1:Suc 1:75 | 32 |
| 5b | 571 | 204 | 0.08 |  | 40 |
| 6a | 473 | 207 | 0.07 | J1:Suc 1:100 | 33 |
| 6b | 907 | 216 | 0.13 |  | 64 |
| 7a | 782 | 214 | 0.11 | J1:Suc 1:500 | 55 |
| 7b | 773 | 221 | 0.11 |  | 54 |

Table 4 vs Table 3 shows that amount of dissolved J1 after 15 seconds is more or less the same when water is used instead of a 5% glucose solution. The more important parameter seems to be amount of sucrose in the freeze-dried vials. The results with J1:sucrose ratio ≤1:50 appear more consistent than the results with higher J1:sucrose ratios.

Example 6. Stability Test of J1:Tert-Butanol Solution

Stability of the solution containing J1 and tert-butanol:water, 1:1 (v/v), was tested. A solution comprising tert-butanol:water 1:1 (v/v) and J1 at a concentration of 1 mg/ml, was left at room temperature for 5 days. The amount of J1 was measured by HPLC and the signal decreased for 97.2% to 85.5%, i.e. a decrease of 11.7%. A similar experiment, where J1 was dissolved in an acidic ethanol-water solution provided a degradation that appeared much more rapid.

Example 7. Dosage Regimen of Preparations of the Invention

The lyophilized pharmaceutical preparations of the present invention, comprising melphalan flufenamide hydrochloride (J1) and sucrose are tested clinically. Patients with advanced malignancy in good performance status, with preserved major organ functions and who are not amendable to standard anticancer therapy but in need of medical treatment, will be enrolled in the study. Initially an accelerated dose titration design is chosen in order to minimise the number of patients treated below biologically active level, which reduce their chances for therapeutic benefit. One patient will be treated at each dose level until a dose limiting toxicity is observed. The study then switches to a conservative design with cohorts of 3 to 6 patients per dose level until maximum tolerated dose is reached.

The starting dose for the study will be a fixed dose 25 mg J1 (approximately 14 mg/m$^2$) which represents in equimolar terms a melphalan dose of 14 mg or 8 mg/m$^2$. The doses will be escalated/reduced according to the toxicity observed, following a pre-defined dosing schedule. The dose escalating regimen is based on the wish and need to as rapidly as possible provide therapeutic benefit to the individual patients whilst taken due consideration in protecting him/her against untoward toxicity. J1 solution will be administered as an iv infusion every 3$^{rd}$ week for 3 to 6 treatment cycles depending on tolerance and tumour response.

All patients will receive the J1 solution as a 30 minutes iv infusion on day 1 each treatment cycle, with 21 days between treatments and with the possibility to be postponed up to 3 weeks waiting for clinically relevant adverse events to return to grade 1 or less. The patients are planned to receive at least 3 treatment cycles. The patients will return to the clinic for safety checks day 8, 10-12, 15 and 21 each cycle. The schedule of events will be repeated each treatment cycle up to 6 treatment cycles, depending on observed toxicity and tumour response.

Treatment Administration

All patients in this study are planned to receive at least 3 treatment cycles with 21 days between treatment administrations. For patients with stable disease or objective tumour remission and tolerable toxicity at the end of cycle 3, the treatment can be extended for another 3 cycles within the study at the discretion of the investigator. Thereafter the patient goes off study. The study treatment will be administered via a central venous catheter, which will be implanted/inserted according standard clinical routines. J1 concentrate will be diluted by the pharmacy in 250 ml 5% glucose. The infusion tubing set should be pre-filled with 5% glucose. The time from preparation to end of infusion should not exceed 60 minutes, i.e. the infusion should start as soon as possible, but not later than 30 minutes from preparation and should be administered as a 30 minute central iv infusion. Prophylactic treatment with the anti-emetic drug (e.g. Navoban; 5 mg iv and Betapred; 4 mg iv) prior to J1 solution administration is recommended. Subsequent anti-emetic drugs against delayed emesis will be administered at the discretion of the investigator. The patients will stay in the clinic for at least 2 hours after stop of study drug administration. Typically, the starting dose for phase IIa will be 50 mg.

Tumour Response

Tumour response will be evaluated at baseline and/or every 3 or 9 weeks/3$^{rd}$ treatment cycle.

At baseline, tumour lesions will be categorized as follows:

| | |
|---|---|
| Measurable | Lesions that can be accurately measured in at least one dimension (longest diameter to be recorded) as ≥20 mm with conventional techniques or as ≥10 mm with spiral CT scan or MRI. |
| Non measurable | All other lesions, including small lesions (longest diameter <20 mm with conventional techniques or <10 mm with spiral CT scan or MRI) and truly non-measurable lesions (i.e. bone lesions, leptomeningeal disease, ascites, pleural/pericardial effusion, inflammatory breast disease, lymphangitis cutis/pulmonis, abdominal masses that are not confirmed and followed by imaging techniques, and cystic lesions). |

Measurable lesions up to a maximum of 5 lesions per organ and 10 lesions in total, representative of involved organs, should be identified as target lesions and will be recorded and measured at baseline. Target lesions should be selected on the basis of their size (those with the longest diameters) and their suitability for accurate repetitive measurements. A sum of the longest diameter for all target lesions will be calculated and reported as the baseline sum longest diameter. The baseline sum longest diameter will be used as the reference by which to characterize the objective tumour response.

All other lesions (or sites of disease) should be identified as non-target lesions and should also be recorded at baseline. Measurements of these lesions are not required, but the presence or absence of each should be noted throughout the follow-up.

Response Criteria for Evaluation of Target Lesions

| | |
|---|---|
| Complete response (CR) | The disappearance of all target lesions. |
| Partial response (PR) | At least a 30% decrease in the sum of the longest diameter of target lesions, taking as reference the baseline sum longest diameter. |
| Stable disease (SD) | Neither sufficient shrinkage to qualify for partial response, nor sufficient increase to qualify for progressive disease, taking as reference the smallest sum longest diameter since the treatment started. |
| Progressive disease (PD) | At least a 20% increase in the sum of the longest diameter of target lesions, taking as reference the smallest sum longest diameter recorded since the treatment started or the appearance of one or more new lesions. |

Response Criteria for Evaluation of Non-Target Lesions

| | |
|---|---|
| Complete response (CR) | The disappearance of all non-target lesions and normalization of tumour marker level. |
| Stable disease (SD) | The persistence of one or more non-target lesion(s) and/or the maintenance of tumour marker level above the normal limits. |
| Progressive disease (PD) | The appearance of one or more new lesions and/or unequivocal progression of existing non-target lesions. |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for preparing a lyophilized pharmaceutical preparation that is directly soluble in a physiologically acceptable aqueous solution, said pharmaceutical preparation comprising melphalan flufenamide or a pharmaceutically acceptable salt thereof comprising the steps of:
   (a) producing a solution containing melphalan flufenamide or a pharmaceutically acceptable salt thereof, an organic solvent and water by:
      (i) dissolving melphalan flufenamide or a pharmaceutically acceptable salt thereof in an organic solvent or a mixture of an organic solvent and water; and
      (ii) if an organic solvent is used in step (i), combining the solution obtained in step (a)(i) with water;
   (b) combining the solution produced in step (a) with sucrose to obtain an aqueous solution of melphalan flufenamide or a pharmaceutically acceptable salt and sucrose in the organic solvent and water at a weight ratio (w/w) of melphalan flufenamide or pharmaceutically acceptable salt thereof to sucrose from about 1:25 to about 1:75; and
   (c) subjecting the aqueous solution obtained in step (b) to lyophilization,
   such that a lyophilized pharmaceutical preparation that is directly soluble in a physiologically acceptable aqueous solution and comprises melphalan flufenamide or a pharmaceutically acceptable salt thereof is obtained.

2. The method of claim 1, wherein:
   step (a) comprises producing a solution containing melphalan flufenamide hydrochloride (J1), an organic solvent and water by:
      (i) dissolving J1 in an organic solvent or a mixture of an organic solvent and water; and
      (ii) if an organic solvent is used in step (i), combining the solution obtained in step (a)(i) with water;
   step (b) comprises combining the solution produced in step (a) with sucrose to obtain an aqueous solution of J1 and sucrose in the organic solvent and water at a weight ratio (w/w) of J1 to sucrose from about 1:25 to about 1:75; and
   step (c) comprises subjecting the aqueous solution obtained in step (b) to lyophilization.

3. The method of claim 2, wherein step (b) comprises combining the solution produced in step (a) with sucrose to obtain an aqueous solution of J1 and sucrose in the organic solvent and water at a weight ratio (w/w) of J1 to sucrose of about 1:50.

4. The method of claim 2, wherein step (a)(i) comprises dissolving J1 in an organic solvent.

5. The method of claim 4, wherein the organic solvent is tert-butanol.

6. The method of claim 5, wherein the solution produced in step (a) has a volume ratio of tert-butanol and water of about 1:1.

7. The method of claim 4, wherein step (a)(ii) comprises diluting the solution obtained in (a)(i) with water to achieve a J1 concentration of about 0.2-3.0 mg/ml.

8. The method of claim 7, wherein the organic solvent is tert-butanol.

9. The method of claim 8, wherein the solution produced in step (a) has a volume ratio of tert-butanol and water of about 1:1.

10. The method of claim 3, wherein step (a)(i) comprises dissolving J1 in an organic solvent.

11. The method of claim 10, wherein the organic solvent is tert-butanol.

12. The method of claim 11, wherein the solution produced in step (a) has a volume ratio of tert-butanol and water of about 1:1.

13. The method of claim 10, wherein step (a)(ii) comprises diluting the solution obtained in (a)(i) with water to achieve a J1 concentration of about 0.2-3.0 mg/ml.

14. The method of claim 13, wherein the organic solvent is tert-butanol.

15. The method of claim 14, wherein the solution produced in step (a) has a volume ratio of tert-butanol and water of about 1:1.

16. The method of claim 2, wherein step (a)(i) comprises dissolving J1 in a mixture of an organic solvent and water.

17. The method of claim 16, wherein the organic solvent is tert-butanol.

18. The method of claim 17, wherein the volume ratio of tert-butanol and water in the mixture is about 1:1.

19. The method of claim 3, wherein step (a)(i) comprises dissolving J1 in a mixture of an organic solvent and water.

20. The method of claim 19, wherein the organic solvent is tert-butanol.

21. The method of claim 20, wherein the volume ratio of tert-butanol and water in the mixture is about 1:1.

22. The method of claim 5, wherein the sucrose combined with the solution produced in step (a) is in the form of an aqueous solution.

23. The method of claim 6, wherein the sucrose combined with the solution produced in step (a) is in the form of an aqueous solution.

24. The method of claim 14, wherein the sucrose combined with the solution produced in step (a) is in the form of an aqueous solution.

25. The method of claim 15, wherein the sucrose combined with the solution produced in step (a) is in the form of an aqueous solution.

26. The method of claim 1, in which sucrose is the sole excipient in the solution lyophilized in step (c).

27. The method of claim 5, in which sucrose is the sole excipient in the solution lyophilized in step (c).

28. The method of claim 6, in which sucrose is the sole excipient in the solution lyophilized in step (c).

29. The method of claim 14, in which sucrose is the sole excipient in the solution lyophilized in step (c).

30. The method of claim 15, in which sucrose is the sole excipient in the solution lyophilized in step (c).

31. The method of claim 1, wherein the melphalan flufenamide or a pharmaceutically acceptable salt thereof is in the form of a pharmaceutically acceptable salt.

32. The method of claim 31, in which sucrose is the sole excipient in the solution lyophilized in step (c).

33. The method of claim 31, in which the organic solvent is tert-butanol.

34. The method of claim 32, in which the organic solvent is tert-butanol.

* * * * *